US007035370B2

(12) United States Patent
Flohr et al.

(10) Patent No.: US 7,035,370 B2
(45) Date of Patent: Apr. 25, 2006

(54) METHOD FOR EXAMINING A BODY REGION OF AN EXAMINATION OBJECT, WHICH BODY REGION PERFORMS A PERIODIC MOVEMENT, AND CT APPARATUS FOR CARRYING OUT SUCH A METHOD

(75) Inventors: Thomas Flohr, Uehlfeld (DE); Bernd Ohnesorge, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/895,075

(22) Filed: Jul. 21, 2004

(65) Prior Publication Data

US 2005/0058238 A1  Mar. 17, 2005

(30) Foreign Application Priority Data

Jul. 21, 2003  (DE)  ................................ 103 33 074

(51) Int. Cl.
*A61B 6/00*  (2006.01)
(52) U.S. Cl. ........................................... 378/8; 378/95
(58) Field of Classification Search .............. 378/4–20, 378/95
See application file for complete search history.

(56) References Cited

U.S. PATENT DOCUMENTS

| 6,504,893 | B1 | 1/2003 | Flohr et al. ...................... 378/8 |
| 6,504,894 | B1 * | 1/2003 | Pan et al. ....................... 378/8 |
| 6,763,082 | B1 * | 7/2004 | Ozaki ............................. 378/8 |
| 6,865,250 | B1 * | 3/2005 | Londt et al. .................... 378/8 |
| 2003/0007593 | A1 | 1/2003 | Heuscher et al. ............... 378/4 |
| 2005/0175141 | A1 * | 8/2005 | Bruder et al. ................... 378/8 |

FOREIGN PATENT DOCUMENTS

DE  198 42 238 A1  4/2000

* cited by examiner

Primary Examiner—David V. Bruce
Assistant Examiner—Jurie Yun
(74) Attorney, Agent, or Firm—Harness, Dickey & Pierce, P.L.C.

(57) ABSTRACT

A method is for examining a body region of an examination object, which body region performs a periodic movement in the form of a sequence of movement cycles including phases of the periodic movement. The method preferably uses a CT apparatus with a radiation source for generating a radiation that penetrates through the examination object at different projection angles, and a detector system for the radiation emerging from the radiation source. An image, at least of the body region that performs the periodic movement, is determined by way of an electronic computing device from the output data of the detector system, which correspond to the detected radiation and are used as measurement data. In this case, it is provided that, from a number $n \geq 1$ of preferably successive movement cycles, data intervals are taken with respect to the same phase of the periodic movement. The overall length of these intervals produces at least one reconstruction interval that suffices for determining an image. The number of movement cycles from which the data intervals of a reconstruction interval originate increases as the frequency of the periodic movement increases, and the length of the data intervals falls as the frequency of the periodic movement increases.

23 Claims, 3 Drawing Sheets

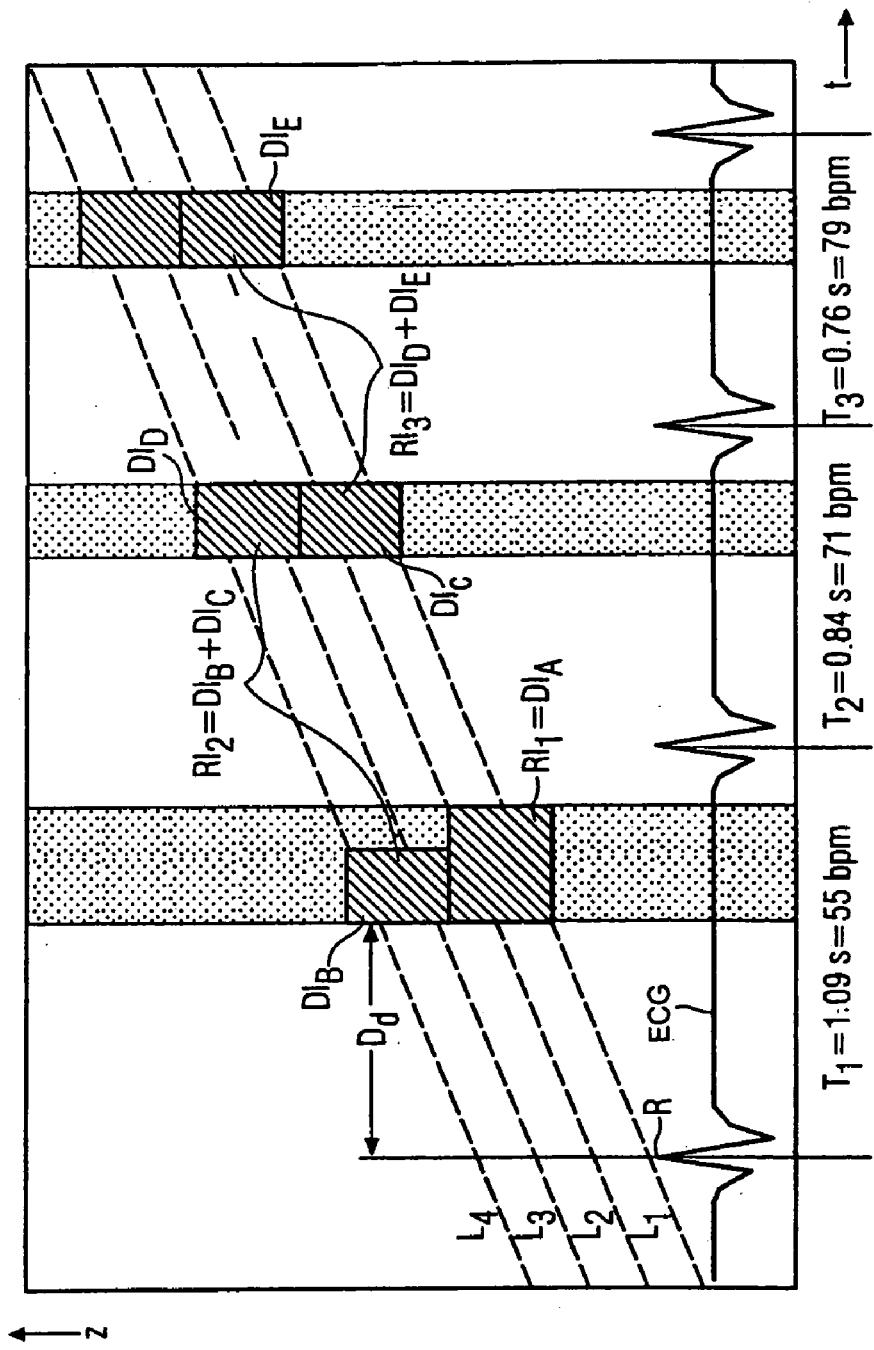

METHOD FOR EXAMINING A BODY REGION OF AN EXAMINATION OBJECT, WHICH BODY REGION PERFORMS A PERIODIC MOVEMENT, AND CT APPARATUS FOR CARRYING OUT SUCH A METHOD

The present application hereby claims priority under 35 U.S.C. §119 on German patent application number DE 103 33 074.7 filed Jul. 21, 2003, the entire contents of which are hereby incorporated herein by reference.

FIELD OF THE INVENTION

The invention generally relates to a method for examining a body region of an examination object. The body region preferably is one which performs a periodic movement in the form of a sequence of movement cycles including phases of the periodic movement. Further, this method may be performed by use of a CT apparatus with a radiation source for generating a radiation that penetrates through the examination object at different projection angles, and a detector system for the radiation emerging from the radiation source. An image at least of the body region, e.g. of a heart, that performs the periodic movement may be determined by way of an electronic computing device from the output data of the detector system, which correspond to the detected radiation and are used as measurement data. The invention additionally generally relates to a CT apparatus for carrying out such a method.

BACKGROUND OF THE INVENTION

It is known to perform ECG-controlled CT multirow spiral recordings of the heart. In this case, the patient's ECG signal is concomitantly recorded during the recording of the multirow spiral data record. The ECG signal is used in order later, during the image reconstruction of CT images, to select measurement data. Thereby, for each image, a contribution is made only by measurement data which have been recorded in specific phases of the cardiac cycle that can be chosen by the user.

Thus, by way of example, there may be the requirement to reconstruct images in the diastolic resting phase. This can be done in order to obtain an imaging of the coronary arteries that is not disturbed by motion artifacts. The temporal positions of the R spikes can be used as a simple reference point in the ECG signal. For each CT image, the intention then is to use for image reconstruction e.g. only data which have been recorded in a certain time window with a specific relative spacing from the preceding R spike (e.g. measured in % of the duration of the RR interval of the ECG signal).

Such a recording technique with associated multirow spiral image reconstruction is the subject matter of DE 198 42 238 A1.

In order that the examination object to be imaged can be expediently reconstructed, measurement data records at successive projection angles $\alpha$ are necessary which extend in parallel geometry over a reconstruction interval of at least 180° (reconstruction interval $[\alpha_{min}, \alpha_{max}] \geq 180°$). Depending on the desired temporal resolution in an image, the total reconstruction interval $[\alpha_{min}, \alpha_{max}]$ is composed of n data intervals which have been recorded in successive cardiac cycles with respect in each case to the same relative cardiac phase, as is illustrated in FIG. 1.

Given a rotation time $T_{rot}$ of the CT scanner of 500 msec, for example, achieving a temporal resolution of 50 msec in the individual image in the best case requires at least n=5 data intervals each of 36° comprising n=5 successive cardiac cycles for image reconstruction. The table advance speed v in the z direction (the z direction is the direction of the longitudinal axis of the patient) during the spiral recording must in this case be chosen to be so small that the multirow detector continues to move by at most a total detector width D during the n successive cardiac cycles. This is because it is only then that each z position of the examination object is irradiated during the n cardiac cycles required for image reconstruction, and all the measurement data required for image reconstruction can be obtained at each z position in the manner revealed in FIG. 2.

At low heart rates, this leads to such small table advance speeds that, during the customary maximum time for a spiral recording given by the patient's breath holding time, only inadequate object lengths can be covered at the required resolution in the z direction (layer thickness). Given a heart rate of 70 beats per minute, n=5 successive cardiac cycles last about 4.3 sec.

Assuming a multirow detector with 4 detector rows which each cover 1 mm in the z direction (layer thickness 1 mm, total detector width D=4 mm), then the detector is permitted to continue to move precisely 4 mm during 4.3 sec. In a customary breath holding phase of 35 sec, it is thus possible to cover at most 32 mm, which is far too little for imaging the heart.

In order to increase the object length that can be covered during a breath holding phase, it is either possible to choose a larger layer thickness (e.g. layer thickness 2.5 mm, total detector width D=4*2.5 mm=10 mm instead of D=4*1 mm=4 mm), or the condition that each z position of the examination object must be irradiated during all n (in this case n=5) cardiac cycles is relinquished. The measurement data required at a specific z position then have to be generated by so-called spiral interpolations—known per se—from measurement data situated remote from the image plane. Both cases (larger layer thickness and lengthier spiral interpolation) result in a loss of sharpness in the z direction, which is undesirable for imaging fine object structures such as e.g. the coronary arteries. Although images with good temporal resolution are then obtained, they have inadequate spatial resolution.

SUMMARY OF THE INVENTION

An embodiment of the invention is based on an object of designing a method such that an improved spatial resolution can be obtained, and of specifying a CT apparatus for carrying out such a method.

An embodiment of the invention is based on the consideration that, by way of example, in order to image the coronary arteries in the heart's resting phase, it is not necessary absolutely always to obtain the best possible temporal resolution for every heart rate. Further, the time window of relatively small cardiac movement that is available for image reconstruction depends rather on the heart rate: it is larger for low heart rates, and it becomes smaller for high heart rates.

An embodiment of the invention takes account of this through an adaptive choice both of the number of data intervals, i.e. movement cycles, and of the duration of the data intervals. In this case, the number of movement cycles and the length of the data intervals are adapted to the frequency of the periodic movement in such a way that the number of movement cycles from which the data intervals of a reconstruction interval originate increases as the frequency of the periodic movement increases and the length of the data intervals falls as the frequency of the periodic movement increases. Preferably, the product of number of movement cycles and length of the data intervals is at least approximately constant.

Within a specific maximum time, e.g. the breath holding time, it is thus possible to image a sufficient object length (e.g. the heart) with the desired good spatial resolution and sufficient temporal resolution. Consequently, the required spatial resolution for imaging fine structures is provided in all the images and each image nevertheless has a temporal resolution which is adapted to the respective local, i.e. current, heart rate and is sufficient for the relative heart rate.

In the course of the described adaptive choice of the parameters mentioned, when examining the heart in the course of a spiral recording with a fixed table advance speed v, a fixed number n of cardiac cycles is not used for image reconstruction for each image (e.g. always n=5), as in the prior art, rather the number $n_{max}$ of data intervals and thus the number $n_{max}$ of cardiac cycles used for image reconstruction is made dependent on the heart rate during the spiral recording. Few data intervals are used for low heart rates; more data intervals are used as heart rates rise. It thus becomes clear that the temporal resolution in an image which can be achieved in the case of an embodiment of the invention is dependent on the heart rate.

In this case, in accordance with one variant of an embodiment of the invention, account is taken of the local frequency of the movement, that is to say heart rate for example, which is to be understood to be the heart rate currently present in the examination interval respectively considered.

In accordance with one embodiment of the invention, the advance speed is constant; it is chosen such that, during the spiral recording the volume of interest can be scanned during a specific time, e.g. during a breath holding phase, with the desired spatial resolution. In accordance with one variant of the invention, the advance is chosen such that the detector continues to move at most by a specific distance, maximally the total detector width D, during $n_{max}$ successive cardiac cycles.

In order to be able to take account of the movement frequency, in particular the local movement frequency, in a simple manner, variants of the invention provide for a signal corresponding to the periodic movement to be obtained and evaluated in order to determine the frequency and/or the phases of the periodic movement, in the case of which examinations of the heart may involve the electrocardiogram of the living entity examined.

According to an embodiment of the invention, a CT apparatus has program device(s) which in operation during an examination pass, vary the number $n_{max}$ of movement cycles from which the data intervals of a reconstruction interval are taken, in which case, in the case of higher frequency of the periodic movement, the number $n_{max}$ of movement cycles from which the data intervals of a reconstruction interval are taken is chosen to be greater than in the case of lower frequency and the length of the data intervals used for the reconstruction is chosen to be smaller.

The CT apparatus is preferably designed as a spiral CT apparatus having a multirow detector and having a device for determining the frequency and/or the phases of the periodic movement, in the case of which examinations of the heart may involve an electrocardiograph.

The text above makes it clear that an adaptive technique for ECG-controlled CT multirow spiral recording of the heart results, the number of cardiac cycles used for image reconstruction depending on the local heart rate and increasing as the heart rate increases. In this way, in a predetermined maximum time, it is possible to image the desired volume with uniformly good spatial resolution and with temporal resolution that is improved ever further as the heart rate increases.

BRIEF DESCRIPTION OF THE DRAWINGS

A non-limiting exemplary embodiment of the invention is explained in more detail below with reference to the drawings, in which.

DETAILED DESCRIPTION OF THE PREFERRED EMBODIMENTS

Figure 1:
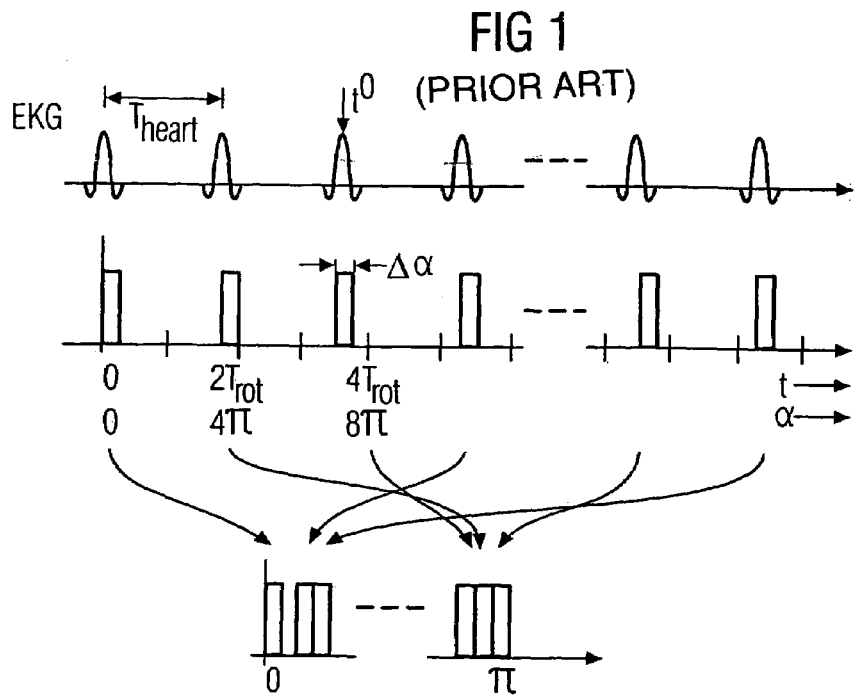
FIGS. 1 and 2—diagrams illustrating methods according to the prior art.
Figure 2:
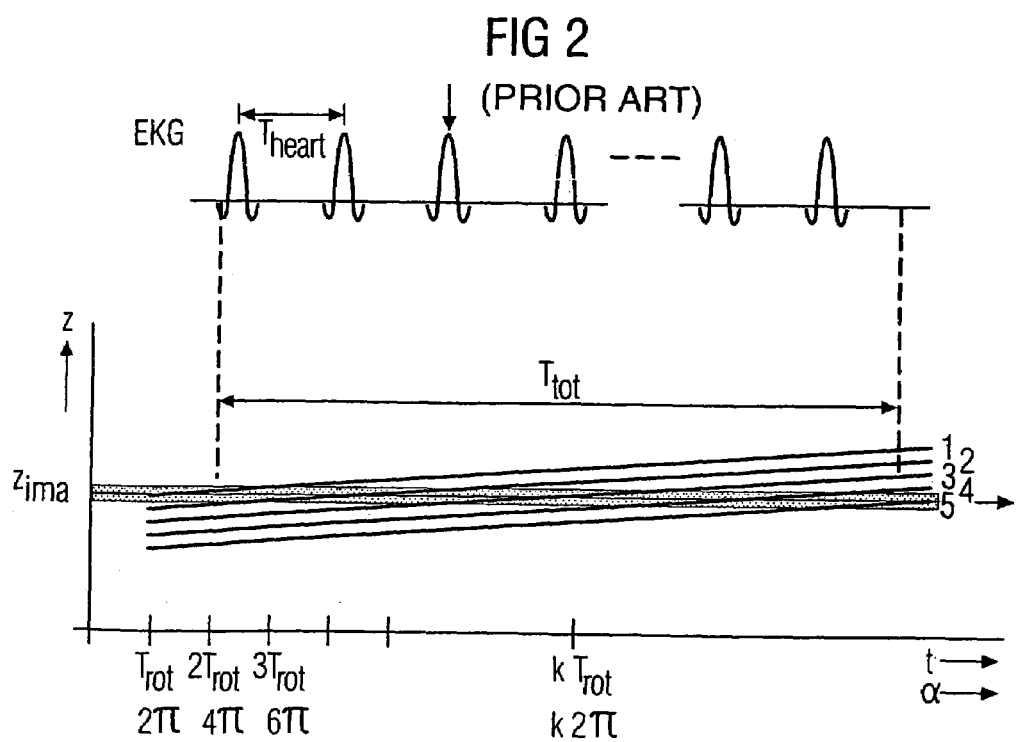
Figure 3:
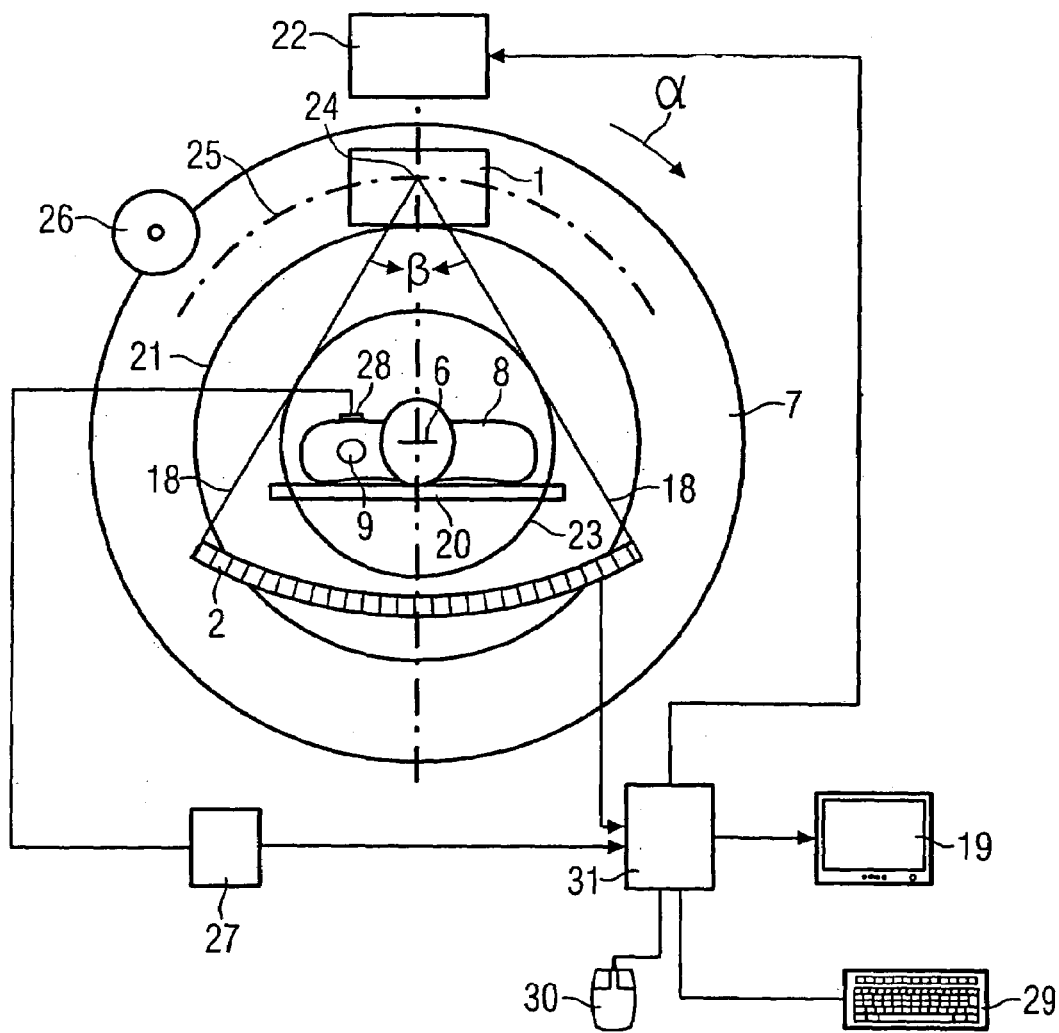
FIG. 3—a view of a CT apparatus serving for carrying out the method according to an embodiment of the invention, FIG. 4—a view of the detector unit of the CT apparatus in accordance with FIG. 3, FIG. 5—a diagram illustrating the mode of operation of the method according to an embodiment of the invention.
Figure 4:
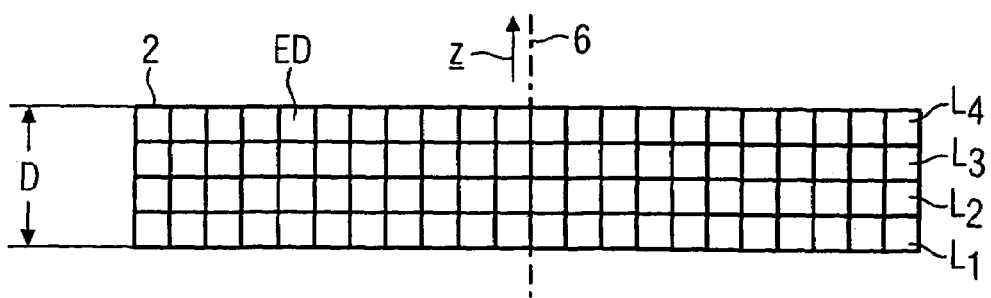

FIGS. 3 and 4 diagrammatically illustrate a diagnostic apparatus, namely a CT apparatus, for carrying out the method according to an embodiment of the invention.

The CT apparatus has a measuring unit including an X-ray source 1, which emits an X-ray beam 18, and a detector unit 2, which is composed of a plurality of rows of individual detectors ED, e.g. 512 individual detectors in each case, succeeding one another in the direction of a rotation axis 6, also referred to as system axis. The focus of the X-ray source 1, from which the X-ray beam 18 emerges, is designated by 24. The examination object, a human patient 8 in the case of the exemplary embodiment illustrated, lies on a supporting table 20, which extends through the measurement opening 21 of an annular carrier 7, the so-called gantry.

In accordance with FIG. 4, the detector unit 2 has a first detector row $L_1$ and a last detector row $L_4$. One or else, as illustrated, a plurality of further detector rows $L_2$ to $L_3$ may be arranged between the first and last detector rows $L_1$ and $L_4$. However, in a manner that is not illustrated, it is also possible for just the first and the last detector row $L_1$ and $L_4$ to be present.

The detector rows $L_1$ to $L_4$ run at right angles to the Z direction, i.e. at right angles to the system axis 6, indicated in dash-dotted fashion in FIG. 4. The extent of the detector system in the direction of the system axis, measured parallel to the system axis 6, is the total detector width designated by D.

On the carrier 7, the X-ray source 1 and the detector unit 2 are fitted opposite one another in such a way that the X-ray beam 18 emerging from the X-ray source 1 impinges on the detector unit 2. The carrier 7 is mounted such that it can rotate about the system axis 6 of the CT apparatus, which represents the system axis, and, for the purpose of scanning the patient 8, rotates at a rotational speed u about the system axis 6. In this case, the X-ray beam 18 emerging from the X-ray source 1 operated by means of a generator device 22 registers a measurement field 23 of circular cross section. The focus 24 of the X-ray source 1 moves on a focus path 25 curved circularly about a centre of rotation located on the system axis 6.

The X-ray beam 18 radiates through the patient 8 and the X-rays arriving at the detector unit 2 are detected during the rotation at a multiplicity of projection angles α and the output data of the individual detectors for each of the detector rows 3 to 5 are combined to form a respective projection associated with the respective projection angle α. Thus, a number of projections corresponding to the number of detector rows 3 to 5 is associated with each projection angle α.

Using the projections recorded during a reconstruction interval, which may include a plurality of data intervals in a manner that is yet to be explained. The projections pass from the detector unit 2 to an electronic computing device 31, and the latter reconstructs a sectional image of the examination object on the basis of algorithms known per se. In order to be able to expediently reconstruct sectional images of the examination object, i.e. of the patient 8, it is necessary to record projections for successive projection angles α which extend over a reconstruction interval, which has to be at least equal to 180° (π) in parallel beam geometry and at least equal to 180°+β in fan beam geometry, where β is the aperture angle of the X-ray beam 18 that is illustrated in FIG. 3 and is also referred to as the fan angle.

As mentioned, the drive 26 assigned to the carrier 7 is suitable for causing the carrier 7 to rotate continuously. Moreover, a further drive (not shown in FIGS. 3 and 4) is provided, which enables a relative displacement of the supporting table 20 and thus of the patient 8, on the one hand, and of the carrier 7 with the measuring unit 1, 2, on the other hand, in the direction of the system axis 6 with a table advance speed v.

It is thus possible to scan three-dimensional regions of the patient 8 in a manner known per se in the form of a spiral recording by virtue of the carrier 7 with the measuring unit 1, 2 rotating continuously and, at the same time, a relative displacement of supporting table 20 and carrier 7 being effected in the direction of the system axis 6 with a table advance speed v.

In order to carry out examinations of the heart or regions near the heart moving with the rhythm of the cardiac action in the body of the patient 8, the CT apparatus in accordance with FIG. 3 additionally has an electrocardiograph 27 known per se, which can be connected to the patient 8 via electrodes, one of which is illustrated in FIG. 3 and designated by 28, and serves for acquiring the ECG signal of the patient 8 in parallel with the examination of the patient 8 by way of the CT apparatus. Preferably digital data corresponding to the ECG signal are fed to the electronic computing device 31.

The electrodes of the electrocardiograph 27 are, if possible, fitted to the body of the patient 8 in such a way that they do not impair the examination of the patient 8.

A keyboard 29 and a mouse 30, which enable the operational control of the CT apparatus, are connected to the electronic computing device 31.

If the intention is to record body parts of the patient 8 which can be kept still, no appreciable problems arise for the recording of the projections. By contrast, the recording of projections of a region that moves periodically, for example, within the patient 8 is critical. An example of such a region that moves periodically is the human heart 9, indicated diagrammatically in FIG. 3.

As is known, the human heart 9 essentially performs a periodic movement. In this case, the periodic movement contains a sequence of cardiac cycles, each of which comprises a movement or beating phase and a subsequent resting or relaxation phase. The relaxation phase has a duration of usually between 500 and 800 ms, and the beating phase has a duration of 200 to 250 ms.

The rotational speed u of the carrier 7 is usually 45 to 120 revolutions/minute. By comparing the rotational speed u with the duration of the relaxation phase of the heart 9, it can thus readily be ascertained that, in the relaxation phase of the heart 9, the carrier 7 rotates through an angle γ of rotation which lies between 135° (500 ms at 45 revolutions/minute) and 576° (800 ms at 120 revolutions/minute).

If the rotational speed u is chosen to be high enough, the carrier 7, during the phase of a cardiac cycle that is respectively to be recorded, e.g. during a resting phase, rotates through an angle which is greater than the required reconstruction interval. Consequently, it is possible, during the phase of a cardiac cycle that is respectively to be recorded, to record the projections required for the reconstruction of a sectional image of the recorded region of the heart 9.

If the heart rate is so high or the phase of the cardiac cycle that is to be recorded is so short that it is not possible to record the projections associated with a complete reconstruction interval during a single cardiac cycle, this may be effected during the phase of a plurality of successive cardiac cycles that is respectively to be recorded. The reconstruction interval is then composed of a plurality of data intervals associated with different cardiac cycles.

As already mentioned, the electrocardiogram of the human heart 9 is recorded during the spiral scan, to be precise in order to be able to determine from it the phases of the cardiac cycles of the human heart 9 that are respectively to be recorded, e.g. the resting phases 13.

An explanation is given below of the fact that the ECG signal is utilized in the case of an embodiment of the invention in order, without losing spatial resolution, to be able to increase the respective temporal resolution of the images in the required manner as the heart rate increases. For this purpose, the electronic computing device on the one hand evaluates the ECG signal and on the other hand, on the basis of the evaluation result, takes from the corresponding measurement data from one or a plurality of preferably successive cardiac cycles, data intervals with respect to the same phase of the periodic movement, the length of which overall produces at least one reconstruction interval sufficient for determining an image. In this case, it adapts the number $n_{max}$ of cardiac cycles and the length of the data intervals to the heart rate in such a way that the product of number $n_{max}$ of cardiac cycles. Further, the length of the data intervals is essentially independent of the heart rate, that is to say at least approximately constant.

In order to carry out an examination by the method according to an embodiment of the invention, the constant table advance speed v of the supporting table 20 during the spiral recording is chosen such that it is possible to cover the volume of interest in a breath-holding phase with the desired spatial resolution in the z direction (e.g. layer thickness 1 mm, total detector width in the case of a 4-row detector D=4 mm). By way of example, if the table advance speed is v=2 mm/sec, then in 35 sec it is thus possible to cover a distance of 70 mm and thus the relevant regions of the coronary arteries.

This complies with the abovementioned condition that the detector is intended to continue to move at most by a specific maximum distance, e.g. by a total detector width D, during $n_{max}$ successive cardiac cycles. From this, the maximum number $n_{max}$ of successive cardiac cycles which can be used for image reconstruction for a given local heart rate is calculated, since, after all, the table advance speed v is fixed, for each heart rate. In the present example, $n_{max}=1$ holds true for heart rates $\leq 60$ beats per minute, $n_{max}=2$ holds true for heart rates of between 60 beats per minute and 90 beats per minute, and $n_{max}=3$ holds true for heart rates of between 90 beats per minute and 120 beats per minute, etc.

Accordingly, the image reconstruction is carried out such that, for each image to be reconstructed, firstly the concomitantly recorded ECG signal is used to determine the local heart rate, i.e. the heart rate which was currently present during the recording of the data at that location in the measurement data at which measurement data were recorded for the z position of the image to be reconstructed.

If, in the present example, the local heart rate is less than 60 beats per minute, only one data segment from a cardiac cycle is used for image reconstruction.

Given a rotation time $T_{rot}$ of the carrier 7 of 500 msec, the temporal resolution in this image is then 250 msec. This is sufficient owing to the low heart rate for an imaging in the diastolic phase.

This temporal resolution is not sufficient at heart rates of between 60 beats per minute and 90 beats per minute. Since it is possible without impairment of the spatial resolution, however, to use two successive cardiac cycles for image reconstruction and thus in the best case to obtain a temporal resolution of 125 msec, etc.

It thus becomes clear that the image reconstruction technique according to an embodiment of the invention generates images with uniformly good spatial resolution and temporal resolution that is improved ever further as the heart rate increases.

The procedure according to an embodiment of the invention is illustrated diagrammatically using an example in FIG. 5, firstly the z position swept over by the detector rows $L_1$ to $L_4$ and secondly the ECG signal being plotted against time t in the diagram in accordance with FIG. 5.

As becomes clear from the linear profiles of the z position associated with the individual detector rows $L_1$ to $L_4$ against time t, the advanced speed v is constant. As additionally becomes clear from the time intervals $T_1$ to $T_3$ between the r spikes of the ECG signal, the heart rate increases in the case of the example illustrated, to be precise from 55 beats per minute (bpm) to 79 beats per minute.

While $n_{max}=1$ holds true during the first cardiac cycle in FIG. 5, as explained above, and, consequently, the entire reconstruction interval $RI_1$ required to reconstruct an image includes only a single data interval $DI_a$, which can be recorded in its entirety during the cardiac cycle with the period duration $T_1$, this is no longer possible for the following cardiac cycles.

Here the increase in the heart rate means that $n_{max}=2$ holds true, which means that the reconstruction interval $RI_2$ of the following image includes two data intervals $DI_B$ and $DI_C$, of which one was recorded during the first cardiac cycle with the period duration $T_1$ and the other was recorded during the second cardiac cycle with the period duration $T_2$ illustrated in FIG. 5.

The same also holds true correspondingly for the following image, which is based on a reconstruction interval $RI_3$ comprising two data intervals $DI_C$ and $DI_D$, the first being recorded during the second cardiac cycle with the period duration $T_2$ and the second being recorded during the third cardiac cycle with the period duration $T_3$ illustrated in FIG. 5.

If the heart rate then accelerates further and exceeds 90 beats per minute, a transition to $n_{max}=3$ would take place, in a manner that is not illustrated, and the data intervals on which the reconstruction interval of an image is based would accordingly originate from three successive cardiac cycles.

It thus becomes clear that, in the case of the method according to an embodiment of the invention, the temporal resolution likewise advantageously increases as the heart rate increases, since the data intervals on which the reconstruction of an image is based become ever shorter in the course of adaptive matching of $n_{max}$ oriented to the heart rate. It becomes clear from the above explanations that the spatial resolution of the images generated is not affected.

As is illustrated in FIG. 5, in order to reconstruct a 3D image in a specific phase of the cardiac cycle (e.g. the diastole, i.e. resting phase), all that are used for the reconstruction are projections of this phase which were recorded during each cardiac cycle in a time segment corresponding to the specific phase, the time segment beginning with a specific delay time $D_d$ after the last R-spike of the ECG.

The delay time $D_d$ and the maximum permissible duration of the time segment are determined retrospectively by the electronic computing device 31 in that the latter determines the average value of the duration of the RR intervals $T_{RR}$ from a preselectable number of preceding RR intervals and from this determines the delay time $D_d$ and duration of the time segment as preselectable percentages or fractions of said average value. As an alternative, the delay time $D_d$ and the duration of the time segment may also be preselected as time durations, for example in milliseconds.

The table advance speed v is set by the electronic computing device 31 taking account of the average value of the duration of the RR intervals $T_{RR}$ from a preselectable number of preceding RR intervals such that the displacement of the supporting table 20 in the direction of the system axis 6, the displacement occurring during a reconstruction interval RI or data interval DI, i.e. the movement of the measuring unit 1, 2 and of the patient 8 relative to one another in the direction of the system axis 6, does not exceed a total detector width D (see FIG. 4). The regions of the patient 8 which are covered by successive reconstruction intervals RI or data intervals DI thus overlap in the direction of the system axis 6 or adjoin one another without any gaps in the limiting case. Consequently, the entire volume of the patient 8 scanned in the direction of the system axis can be covered by sectional images without any gaps.

Instead of the ECG signal, it is also possible to use other physiological parameters or signals which provide information about the respectively present phase of the cardiac cycle e.g. heart wall movement or stethoscopic heartbeat analysis.

An embodiment of the invention is explained above using the example of examinations of the heart. However, other body regions that are moved periodically can also be examined by the method according to an embodiment of the invention.

In connection with the above description of embodiments of the invention, a third-generation CT apparatus is used, i.e. the X-ray source and the detector unit are moved jointly about the system axis during image generation. However, the embodiments of invention can also be used in connection with CT apparatuses of other generations, e.g. fourth-generation CT apparatuses, in which only the X-ray source is moved about the system axis and interacts with a stationary detector ring.

Moreover, in addition to being used in computer tomography, embodiments of the invention can also be used in other imaging methods that work with penetrating radiation.

The embodiments of the invention are explained above on the basis of a medical application. However, the embodiments of the invention can also be used outside medicine.

Any of the aforementioned methods may be embodied in the form of a program. The program may be stored on a computer readable media and is adapted to perform any one of the aforementioned methods when run on a computer. Thus, the storage medium or computer readable medium, is adapted to store information and is adapted to interact with a data processing facility or computer to perform the method of any of the above mentioned embodiments.

The storage medium may be a built-in medium installed inside a computer main body or removable medium arranged so that it can be separated from the computer main body. Examples of the built-in medium include, but are not limited to, rewriteable involatile memories, such as ROMs and flash memories, and hard disks. Examples of the removable medium include, but are not limited to, optical storage media such as CD-ROMs and DVDS; magneto-optical storage media, such as MOs; magnetism storage media, such as floppy disks (trademark), cassette tapes, and removable hard disks; media with a built-in rewriteable involatile memory, such as memory cards; and media with a built-in ROM, such as ROM cassettes.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for examining a body region, which performs a periodic movement in the form of a sequence of movement cycles including phases of the periodic movement, of an examination object, the method comprising:
   using a diagnostic apparatus with a radiation source to generate a radiation that penetrates through the examination object at different projection angles;
   using a detector system for detecting the radiation emerging from the radiation source; and
   determining data intervals at which data is taken using an electronic computing device, from a number $n \geq 1$ of successive movement cycles, with respect to the same phase of the periodic movement, the length of the data intervals producing at least one reconstruction interval that suffices for determining an image of at least the body region that performs the periodic movement from output data of the detector system which correspond to the detected radiation, wherein the number of movement cycles from which the data intervals of a reconstruction interval are taken varies during an examination pass, and, wherein in the case of higher frequency of the periodic movement, the number of movement cycles from which the data intervals of a reconstruction interval are determined is relatively greater than in the case of lower frequency and the length of the data intervals used for the reconstruction is relatively smaller.

2. The method as claimed in claim 1, wherein the number of movement cycles and the length of the data intervals are adapted to the frequency of the periodic movement in such a way that the product of number of movement cycles and length of the data intervals is at least approximately constant.

3. The method as claimed in claim 1, wherein the radiation source for obtaining the measurement data is rotateable about a system axis and the length of a data interval is $\leq 180°$.

4. The method as claimed in claim 1, wherein the radiation source for obtaining the measurement data is rotateable about a system axis and the length of a reconstruction interval is $\geq 180°$.

5. The method as claimed in claim 1, wherein the current frequency of the movement is used for determining the number of movement cycles.

6. The method as claimed in claim 1, wherein, in the course of obtaining the measurement data, an advance is produced in the direction of the system axis between the radiation source and the detector system, on the one hand, and the examination object, on the other hand, the advance speed at which the advance is effected being constant.

7. The method as claimed in claim 1, wherein, in the course of obtaining the measurement data, an advance is produced in the direction of the system axis between the radiation source and the detector system, on the one hand, and the examination object, on the other hand, the advance during the number of movement cycles being at most equal to the extent of the detector system in the direction of the system axis.

8. The method as claimed in claim 1, wherein a signal corresponding to the periodic movement is obtained and evaluated in order to determine at least one of the frequency and the phases of the periodic movement.

9. The method as claimed in claim 8, wherein a heart of a living entity is examined in the body region and an electrocardiogram of the living entity is provided as a signal corresponding to the periodic movement of the heart.

10. A CT apparatus, comprising:
    a radiation source for generating a radiation that penetrates through an examination object within a body region at different projection angles, the examination object performing periodic movements;
    a detector system for detecting the radiation emerging from the radiation source;
    an electronic computing device for reconstruction of sectional images from output data of the detector system; and
    program means for, from a number $n \geq 1$ of successive movement cycles, determining data intervals with respect to the same phase of the periodic movement, the overall length of which produces at least one reconstruction interval sufficient for determining an image, and for, in operation during an examination pass, varying the number of movement cycles from which the data intervals of a reconstruction interval are taken, wherein, in the case of higher frequency of the periodic movement, the number of movement cycles from which the data intervals of a reconstruction interval are determined is chosen to be relatively greater than in the case of lower frequency and the length of the data intervals used for the reconstruction is chosen to be relatively smaller.

11. The CT apparatus as claimed in claim 10, wherein the program means are for simulating the method wherein the number of movement cycles and the length of the data intervals are adapted to the frequency of the periodic movement in such a way that the product of number of movement cycles and length of the data intervals is at least approximately constant.

12. The method as claimed in claim 2, wherein the radiation source for obtaining the measurement data is rotateable about a system axis and the length of a data interval is $\leq 180°$.

13. The method as claimed in claim 2, wherein the radiation source for obtaining the measurement data is rotateable about a system axis and the length of a reconstruction interval is ≧180°.

14. A method for examining a body region, which performs a periodic movement in the form of a sequence of movement cycles including phases of the periodic movement, of an examination object, the method comprising:
   generating a radiation that penetrates through the examination object at different projection angles;
   detecting the radiation emerging from the radiation source; and
   determining data intervals at which data is taken, from a number n≧1 of successive movement cycles, with respect to the same phase of the periodic movement, the length of the data intervals producing at least one reconstruction interval that suffices for determining an image of at least the body region that performs the periodic movement from the detected radiation, wherein the number of movement cycles from which the data intervals of a reconstruction interval are taken varies during an examination pass, and, wherein in the case of higher frequency of the periodic movement, the number of movement cycles from which the data intervals of a reconstruction interval are determined is relatively greater than in the case of lower frequency and the length of the data intervals used for the reconstruction is relatively smaller.

15. The method as claimed in claim 14, wherein the number of movement cycles and the length of the data intervals are adapted to the frequency of the periodic movement in such a way that the product of number of movement cycles and length of the data intervals is at least approximately constant.

16. The method as claimed in claim 14, wherein the radiation source for obtaining the measurement data is rotateable about a system axis and the length of a data interval is ≦180°.

17. The method as claimed in claim 14, wherein the radiation source for obtaining the measurement data is rotateable about a system axis and the length of a reconstruction interval is ≧180°.

18. The method as claimed in claim 14, wherein the current frequency of the movement is used for determining the number of movement cycles.

19. The method as claimed in claim 14, wherein, in the course of obtaining the measurement data, an advance is produced in the direction of the system axis between the radiation source and the detector system, on the one hand, and the examination object, on the other hand, the advance speed at which the advance is effected being constant.

20. The method as claimed in claim 14, wherein, in the course of obtaining the measurement data, an advance is produced in the direction of the system axis between the radiation source and the detector system, on the one hand, and the examination object, on the other hand, the advance during the number of movement cycles being at most equal to the extent of the detector system in the direction of the system axis.

21. The method as claimed in claim 14, wherein a signal corresponding to the periodic movement is obtained and evaluated in order to determine at least one of the frequency and the phases of the periodic movement.

22. The method as claimed in claim 21, wherein a heart of a living entity is examined in the body region and an electrocardiogram of the living entity is provided as a signal corresponding to the periodic movement of the heart.

23. An apparatus for examining a body region, which performs a periodic movement in the form of a sequence of movement cycles including phases of the periodic movement, of an examination object, the apparatus comprising:
   means for generating a radiation that penetrates through the examination object at different projection angles;
   means for detecting the radiation emerging from the radiation source; and
   means for determining data intervals at which data is taken, from a number n≧1 of successive movement cycles, with respect to the same phase of the periodic movement, the length of the data intervals producing at least one reconstruction interval that suffices for determining an image of at least the body region that performs the periodic movement from the detected radiation, wherein the number of movement cycles from which the data intervals of a reconstruction interval are taken varies during an examination pass, and, wherein in the case of higher frequency of the periodic movement, the number of movement cycles from which the data intervals of a reconstruction interval are determined is relatively greater than in the case of lower frequency and the length of the data intervals used for the reconstruction is relatively smaller.

* * * * *